United States Patent
Zhang et al.

(10) Patent No.: US 8,190,232 B2
(45) Date of Patent: May 29, 2012

(54) AUTOMATIC ALIGNMENT OF MAGNETIC RESONANCE IMAGING (MRI) BRAIN SCAN BY ANATOMIC LANDMARKS

(75) Inventors: Li Zhang, Skillman, NJ (US); Carol L. Novak, Newtown, PA (US); Qing Xu, Nashville, TN (US); Chong Chen, Palo Alto, CA (US)

(73) Assignee: Siemens Aktiengesellschaft, Munich (DE)

( * ) Notice: Subject to any disclaimer, the term of this patent is extended or adjusted under 35 U.S.C. 154(b) by 1001 days.

(21) Appl. No.: 12/165,830

(22) Filed: Jul. 1, 2008

(65) Prior Publication Data

US 2009/0093706 A1 Apr. 9, 2009

Related U.S. Application Data

(60) Provisional application No. 60/977,488, filed on Oct. 4, 2007.

(51) Int. Cl.
*A61B 5/05* (2006.01)

(52) U.S. Cl. .................... 600/410; 600/407
(58) Field of Classification Search .............. 600/410, 600/407, 436, 425; 382/128, 154, 177, 203, 382/285, 294
See application file for complete search history.

(56) References Cited

U.S. PATENT DOCUMENTS

| | | | |
|---|---|---|---|
| 2005/0154292 A1* | 7/2005 | Tank | 600/410 |
| 2007/0276219 A1* | 11/2007 | K.N. et al. | 600/410 |
| 2008/0021502 A1* | 1/2008 | Imielinska et al. | 607/1 |
| 2010/0040264 A1* | 2/2010 | Volkau et al. | 382/128 |

OTHER PUBLICATIONS

Wingenter (Skull, facial bone ans sinus radiography).*
Xu et al., "Automatic corpus callosum segmentation for standardized MR brain scanning", Proc. SPIE, vol. 6512, (2007) pp. 65123K.
Chen et al., "Automated Definition of Mid-Sagittal Planes for MRI Brain Scans", Proc. SPIE, vol. 6512, (2007), pp. 65123T.

* cited by examiner

*Primary Examiner* — Tse Chen
*Assistant Examiner* — Joel F Brutus

(57) ABSTRACT

A method to automatically align magnetic resonance (MR) brain scans for diagnostic scan planning, including: acquiring a three-dimensional (3D) localizer image of a patient; selecting a two-dimensional (2D) coronal view and a 2D transverse view from the localizer image; identifying a mid-sagittal plane (MSP) line in each of the coronal and transverse views and calculating a 3D MSP based on the MSP lines; reconstructing the localizer image based on an equation for the 3D MSP to obtain an image of the MSP of the patient's brain; identifying crista galli (CG) and tip of the occipital bone (TOB) in the image of the MSP of the patient's brain; calculating a transformation matrix based on the MSP, CG and TOB in the image and using the transformation matrix to obtain a scan plan for the patient; and outputting the scan plan for the patient.

18 Claims, 8 Drawing Sheets

(A) (B) (C) (D)

(PRIOR ART)

*X axis: from patients' right to left*
*Y axis: from anterior to posterior*
*Z axis: from feet to head*

AUTOMATIC ALIGNMENT OF MAGNETIC RESONANCE IMAGING (MRI) BRAIN SCAN BY ANATOMIC LANDMARKS

CROSS-REFERENCE TO RELATED APPLICATION

This application claims the benefit of U.S. Provisional Application No. 60/977,488, filed Oct. 4, 2007, the disclosure of which is incorporated by reference herein in its entirety.

BACKGROUND OF THE INVENTION

1. Technical Field

The present invention relates to automating brain scanning.

2. Discussion of the Related Art

A typical brain scanning process in most hospitals starts with localizer or scout images acquired by fast MR sequences. This produces a low-resolution image indicating the patient's position within the machine. Then an operator plans a diagnostic scan sequence, which takes a longer time, from the localizer images using anatomic landmarks. However, for different hospitals, departments and operators, different anatomic landmarks may be used to plan the scanning. Even when the same anatomic landmarks are used, due to inter- and intra-operator variation, the scan can be executed in different ways, resulting in inconsistent anatomy on diagnostic images. In addition, the manual process may take several seconds, during which the patient must remain absolutely still. This is inconvenient for the patient (many of whom find the machine claustrophobic) and ties up a very expensive piece of equipment.

To standardize brain scanning, efforts have been made to automate this process by mapping a template with a pre-defined scanning plan to the current scan session. See Young et al. (Stewart Young, Daniel Bystrov, Thomas Netsch, Rene Bergmans, Arianne van Muiswinkel, Fredy Visser, Rudolf Springorum and Jurgen Gieseke "Automated planning of MRI neuro scans", SPIE Medical Imaging 2006: Image Processing, eds J. Reinhardt, J. Pluim, Vol. 6144, pp. 1-8) and Van der Kouwe et al. (Andre J. V. van der Kouwe, Thomas Benner, Bruce Fischl, Franz Schmitt, David H. Salat, Martin Harder, A. Gregory Sorensen, and Anders M. Dale, "On-line automatic slice positioning for brain MR imaging", NeuroImage 27, pp. 222-230, 2005), for example. While anatomic landmarks are routinely used by MR operators to align a diagnostic scan, the alignment calculated by registration based methods may deviate from the desired orientation and position, depending on the spatial relationship between the landmarks used for registration and the landmarks used for scan planning in individual anatomy.

Accordingly, there exists a need for a technique of automatic and standardized planning of brain scans.

SUMMARY OF THE INVENTION

In an exemplary embodiment of the present invention, a method to automatically align magnetic resonance (MR) brain scans for diagnostic scan planning, comprises: acquiring a three-dimensional (3D) localizer image of a patient; selecting a two-dimensional (2D) coronal view and a 2D transverse view from the localizer image; identifying a midsagittal plane (MSP) line in each of the coronal and transverse views and calculating a 3D MSP based on the MSP lines; reconstructing the localizer image based on an equation for the 3D MSP to obtain an image of the MSP of the patient's brain; identifying crista galli (CG) and tip of the occipital bone (TOB) in the image of the MSP of the patient's brain; calculating a transformation matrix based on the MSP, CG and TOB in the image and using the transformation matrix to obtain a scan plan for the patient; and outputting the scan plan for the patient.

The step of identifying an MSP line in each of the coronal and transverse views comprises: detecting a position of the patient's head by fitting an ellipse to each of the coronal and transverse views that maximizes an image gradient magnitude in a boundary region of the ellipse; establishing a symmetrical axis which minimizes a difference between the coronal and transverse views on either side of the symmetrical axis; characterizing low intensity pixels in the coronal and transverse views by using smoothed local differential operators; finding pixels in the coronal and transverse views that form a space between hemispheres in each of the coronal and transverse views; and running a linear regression with robust weights to define a line in each of the coronal and transverse views that best separates the two hemispheres, wherein the line is the MSP line.

The CG is identified by applying an active shape model (ASM) to segment the patient's skull and other anatomic structures around the patient's brain.

The TOB is identified by: searching for low intensity voxels in the segmented skull, wherein the low intensity voxels identify a most convex part of the OB; and tracing boundaries on both sides of the skull to an end of the OB, which is the TOB.

The scan plan for the patient is obtained by multiplying the transformation matrix by a standard slice package. The standard slice package includes a set of image slices with geometry descriptions to be acquired from the patient in a standard coordinate system.

The method further comprises executing the scan plan for the patient.

In an exemplary embodiment of the present invention, a system to automatically align MR brain scans for diagnostic scan planning, comprises: a memory device for storing a program; a processor in communication with the memory device, the processor operative with the program to: acquire a 3D localizer image of a patient; select a 2D coronal view and a 2D transverse view from the localizer image; identify an MSP line in each of the coronal and transverse views and calculate a 3D MSP based on the MSP lines; reconstruct the localizer image based on an equation for the 3D MSP to obtain an image of the MSP of the patient's brain; identify CG and TOB in the image of the MSP of the patient's brain; calculate a transformation matrix based on the MSP, CG and TOB in the image and using the transformation matrix to obtain a scan plan for the patient; and output the scan plan for the patient.

The processor is further operative with the program when identifying an MSP line in each of the coronal and transverse views to: detect a position of the patient's head by fitting an ellipse to each of the coronal and transverse views that maximizes an image gradient magnitude in a boundary region of the ellipse; establish a symmetrical axis which minimizes a difference between the coronal and transverse views on either side of the symmetrical axis; characterize low intensity pixels in the coronal and transverse views by using smoothed local differential operators; find pixels in the coronal and transverse views that form a space between hemispheres in each of the coronal and transverse views; and run a linear regression with robust weights to define a line in each of the coronal and transverse views that best separates the two hemispheres, wherein the line is the MSP line.

The CG is identified by applying an ASM to segment the patient's skull and other anatomic structures around the patient's brain.

The TOB is identified by searching for low intensity voxels in the segmented skull, wherein the low intensity voxels identify a most convex part of the OB; and tracing boundaries on both sides of the skull to an end of the OB, which is the TOB.

The scan plan for the patient is obtained by multiplying the transformation matrix by a standard slice package. The standard slice package includes a set of image slices with geometry descriptions to be acquired from the patient in a standard coordinate system.

The processor is further operative with the program to execute the scan plan for the patient.

In an exemplary embodiment of the present invention, a computer readable medium tangibly embodying a program of instructions executable by a processor to perform method steps to automatically align MR brain scans for diagnostic scan planning, the method steps comprising: acquiring a 3D localizer image of a patient; selecting a 2D coronal view and a 2D transverse view from the localizer image; identifying an MSP line in each of the coronal and transverse views and calculating a 3D MSP based on the MSP lines; reconstructing the localizer image based on an equation for the 3D MSP to obtain an image of the MSP of the patient's brain; identifying CG and TOB in the image of the MSP of the patient's brain; calculating a transformation matrix based on the MSP, CG and TOB in the image and using the transformation matrix to obtain a scan plan for the patient; and outputting the scan plan for the patient.

The step of identifying an MSP line in each of the coronal and transverse views comprises: detecting a position of the patient's head by fitting an ellipse to each of the coronal and transverse views that maximizes an image gradient magnitude in a boundary region of the ellipse; establishing a symmetrical axis which minimizes a difference between the coronal and transverse views on either side of the symmetrical axis; characterizing low intensity pixels in the coronal and transverse views by using smoothed local differential operators; finding pixels in the coronal and transverse views that form a space between hemispheres in each of the coronal and transverse views; and running a linear regression with robust weights to define a line in each of the coronal and transverse views that best separates the two hemispheres, wherein the line is the MSP line.

The CG is identified by applying an ASM to segment the patient's skull and other anatomic structures around the patient's brain. The TOB is identified by: searching for low intensity voxels in the segmented skull, wherein the low intensity voxels identify a most convex part of the OB; and tracing boundaries on both sides of the skull to an end of the OB, which is the TOB.

The scan plan for the patient is obtained by multiplying the transformation matrix by a standard slice package. The standard slice package includes a set of image slices with geometry descriptions to be acquired from the patient in a standard coordinate system.

The method further comprises executing the scan plan for the patient.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

A method to automatically align brain scans for diagnostic scan planning, in accordance with an exemplary embodiment of the present invention, will now be described with reference to the accompanying drawings.

The method requires a three-dimensional (3D) localizer to start the scan planning. The fully automated process provides standardized and reproducible brain scanning for different hospitals, departments and operators, in order to perform disease diagnosis, treatment evaluation and therapy control.

Figure 1:
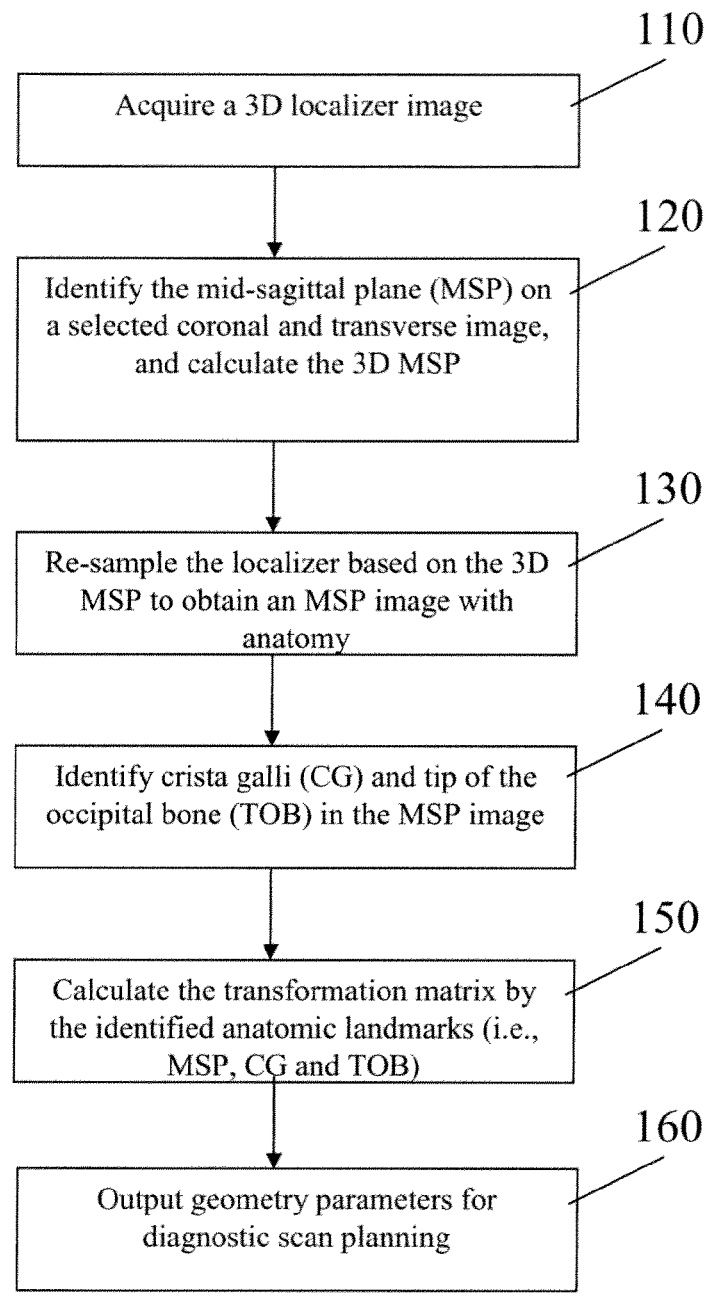
FIG. 1 is a flowchart illustrating a method of landmark based automatic alignment of magnetic resonance (MR) brain scans, in accordance with an exemplary embodiment of the present invention.

The automatic brain alignment algorithm starts with a dedicated three-dimensional (3D) localizer (110). From the 3D localizer, a coronal and a transverse image are selected to identify the mid-sagittal plane (MSP) and the 3D MSP is calculated from the MSP detection results on the selected coronal and transverse images (120). Then the original 3D localizer volume is re-sampled based on the orientation of the MSP to obtain an image with MSP anatomy (130). On the MSP image, two bony structures, the crista galli (CG) and tip of the occipital bone (TOB), are detected by an active shape model (ASM) and a method using directional flow guided by a priori knowledge (140). Finally, a transformation matrix is calculated to transform the localizer coordinates to a standard coordinate system that is defined by anatomical landmarks (150), and the geometry parameters are output for the diagnostic scan planning (160). The workflow of the automatic brain alignment is depicted in FIG. 1, step by step, and a detailed description for each step is given in the following sections.

1.1 MSP Detection

The MSP is a 3D plane separating the two cerebral hemispheres. The MSP can be detected in the localizer volume as a 3D plane using an algorithm that detects the MSP in the entire volume or on every two-dimensional (2D) slice. However, a 3D algorithm is typically much more time consuming than a 2D approach. Moreover, in the brain peripheral area, the separation between the two hemispheres is wider and the MSP is more difficult to distinguish (see FIG. 2A (coronal image from the peripheral brain region) and FIG. 2B (transverse image from the peripheral brain region)) than in the central area (see FIG. 2C (coronal image from the central brain region) and FIG. 2D (transverse image from the central brain region)). As a result, a straightforward 3D MSP detection approach is likely to become more prone to detection errors.

Figure 2:
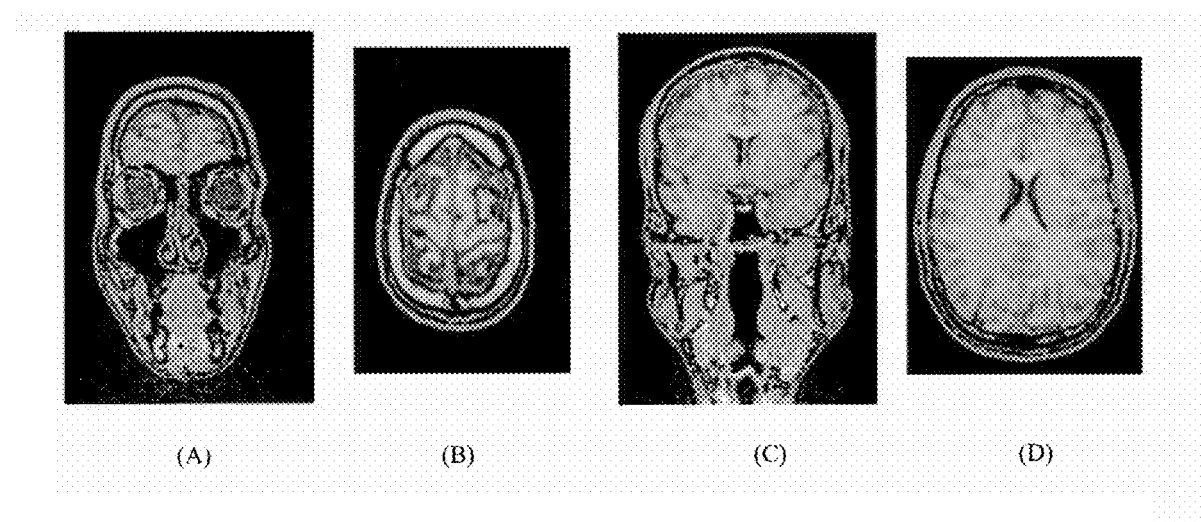
FIG. 2 is a set of images illustrating mid-sagittal plane (MSP) appearance in different brain regions.

In accordance with an exemplary embodiment of the present invention, we have developed a 2D MSP detection algorithm that detects the MSP on a 2D coronal and a 2D transverse image with large brain areas and well-defined MSP features, such as the images of FIGS. 2C and 2D. Subsequently, we calculate the 3D geometry of the MSP from the 2D detection results, yielding an algorithm we refer to as 2D+.

The MSP on a coronal and transverse image is detected using a method similar to the method described in Chen et al. (Hong Chen, Qing Xu, Atilla Kiraly, Li Zhang, and Carol L. Novak, "Automated definition of mid-sagittal planes for MRI brain scans", Proc. SPIE, Medical Imaging, Image Processing, edited by Josien P. W. Pluim, Joseph M. Reinhardt, volume 6512, 65123T, 2007), a copy of which is incorporated by reference herein in its entirety for all purposes. The method first detects the position of the head by finding an ellipse that maximizes the image gradient magnitude in the boundary region of the ellipse. A symmetrical axis is then established which minimizes the difference between the image on either side of the axis. A "ridgeness" calculation is then applied to the image. The "ridgeness" calculation is performed by characterizing low intensity pixels by using smoothed local difference operators. By searching for the minimum "ridgeness", the pixels forming the space between the hemispheres are located in the area adjacent to the symmetrical axis, and a linear regression with robust weights defines a line that best separates the two hemispheres. The 3D geometry of the MSP is calculated based on the two perpendicular 2D MSP lines detected from the coronal and transverse views. It is to be understood that the MSP calculation is done in accordance with the techniques described in Chen et al.

For example, the MSP is computed in the following steps:

1.1.1 3D Representation of Separation Lines in Coronal and Transverse Views

The 3D representation of the MSP is obtained based upon the 2D geometry of the separation lines from the MSP in each slice and the 3D information of each coronal and transverse slice. Let the coordinate vector of the left and upper corner of the slice be $\vec{pos}$, the row vector of the slice, which is the unit vector pointing along the height of the slice, be $\vec{row}$, the column vector of the slice, which is the unit vector pointing along the width of the slice, be $\vec{col}$, and the line in the 2D space of the view be represented as x=ky+c. The 3D parametric representation of the line is $\vec{p}=\vec{p}_0+t\cdot\vec{v}$, where $\vec{p}_0=\vec{pos}+c\cdot\vec{col}$, and $\vec{v}$ is represented as $\alpha\cdot\vec{col}+\beta\cdot\vec{row}$, so that $\alpha/\beta=k$ and $\alpha^2+\beta^2=1$. Values of $\vec{pos}$, $\vec{col}$ and $\vec{row}$ can be retrieved from a Digital Imaging and Communications in Medicine (DICOM) header.

1.1.2 Norm of the MSP

Denote the direction in 3D of two separation lines in coronal and transverse views as $\vec{a}$ and $\vec{b}$. The norm of the MSP is then calculated as $\vec{n}=\vec{a}\times\vec{b}$.

1.1.3 Finding a Point in the MSP

Let $p_1$ and $p_2$ be the closest two points in the two separation lines. The MSP should pass through the mid-point of $p_1$ and $p_2$. To obtain the coordinates of $p_1$ and $p_2$, according to the 3D representation of the lines, let $\vec{p_1}=\vec{s_1}+t_1\cdot\vec{v_1}$ and $\vec{p_2}=\vec{s_2}+t_2\cdot\vec{v_2}$. The distance between $p_1$ and $p_2$ is calculated as $L=\|\vec{p_1}-\vec{p_2}\|^2$. Solve the equation array $$\frac{\partial L}{\partial t_1}=0 \text{ and } \frac{\partial L}{\partial t_2}=0$$

to obtain the value of $t_1$ and $t_2$. Let the mid-point of $\vec{p_1}$ and $\vec{p_2}$ be $\vec{p_m}$. The MSP is then represented as $(\vec{q}-\vec{p_m})\cdot\vec{n}=0$, where $\vec{q}$ is a variable representing a 3D point.

Figure 3:
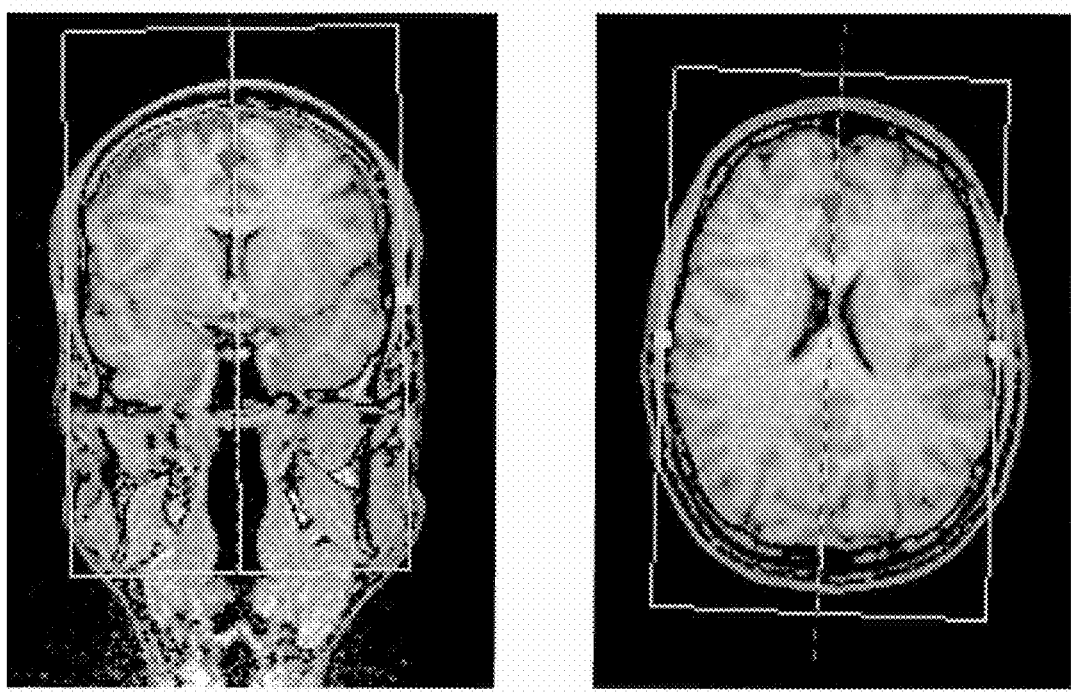
FIG. 3 illustrates identifying the MSP on a coronal image (left) and a transverse image (right), in accordance with an exemplary embodiment of the present invention.

FIG. 3 gives the MSP detection result, as well as a slice package, on a selected coronal (left) and transverse (right) image.

For example, as shown in FIG. 3, the dotted line represents the location of the location of the MSP, and the rectangle with solid boundary is the slice package aligned based on the MSP. The solid line located in the middle of the slice package represents the middle sagittal slice, which is overlapped with the MSP line as the slice package is aligned so that its middle sagittal slice passes through the MSP, and the other sagittal slices are parallel to the MSP.

The coronal and transverse images with large brain area are determined by mapping a template volume with pre-selected images using intensity-based registration. While the intensity-based registration corrects the gross deviation on rotation and translation for the current localizer in order to increase the algorithm reliably for MSP detection, it also transfers the location of pre-selected images from the template so that the MSP can be detected on corresponding slices with similar anatomy from scan to scan and generates consistent results. Moreover, as the MSP lines on a coronal image and a transverse image are perpendicular to each other, the 3D MSP calculated from them in insensitive to small detection errors. The 2D+ method only needs to run the regular 2D approach twice, and thus costs minimal computational effort.

1.2 CG-TOB Detection on Resampled MSP

Once the orientation of the mid-sagittal view is determined by MSP detection, we need to further determine the orientation of coronal and transverse views. Using the orthogonality between sagittal, coronal and transverse views in a scan prescription, the problem can be simplified to determination of the rotation angle on a re-sampled MSP. The rotation angle on the MSP is determined by detecting two bony landmarks: the CG and the TOB.

The re-sampling step reconstructs the MSP in the localizer image from its 3 D representation, i.e. $(\vec{q}-\vec{p_m})\cdot\vec{n}=0$, where $\vec{q}$ represents a 3D point $(X_q, Y_q, Z)$ in the MSP, then an interpolation method, e.g., tri-linear, is used to calculate the voxel intensity for $(X_q, Y_q, Z)$ from the localizer to complete the reconstruction of the MSP.

Figure 4:
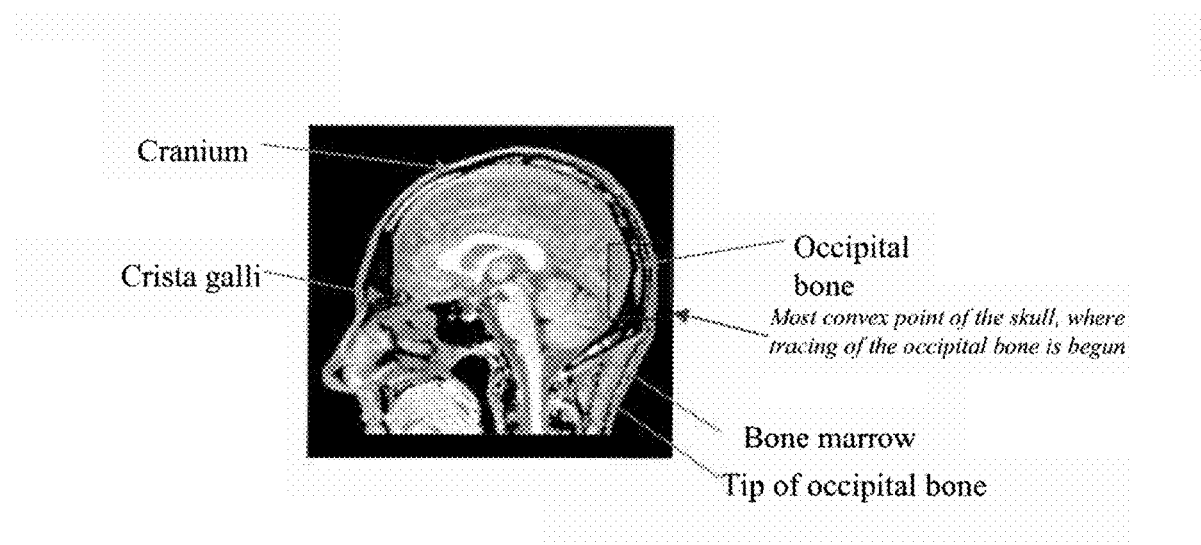
FIG. 4 illustrates identified anatomic landmarks on a re-sampled MSP image, in accordance with an exemplary embodiment of the present invention.

The CG is a triangular bone process articulating with the frontal bone of the cranium (see FIG. 4). The occipital bone is a curved trapezoid structure at the back and lower part of the cranium. The occipital bone appears as a curved narrow band on an MR image passing through the MSP (see FIG. 4), and its bottom end (i.e., the TOB) serves as the other anatomic landmark to determine the in-plane MSP rotation angle.

To detect the two bony landmarks, an ASM is first applied to segment the skull and other bony structures around the brain. The model used in the ASM is trained to fit into the skull around the brain, and its fourth node is located at the CG. As bony structures appear in low intensity in the image acquired by our 3D localizer sequence, the ASM searches the low intensity points along the profile perpendicular to the model, and the result is further improved by weighing the boundary movement with confidence scores.

The ASM result provides the location of the CG by the segmentation of the skull. However, since the ASM works on the intensity distribution on the profiles that are perpendicular to the model and passing through sparsely distributed nodes along the model, the ASM cannot accurately locate the position of the TOB (see FIG. 4), although the ASM result approximates the location of the skull including the occipital bone.

The TOB is detected by a method using a directional flow guided by a priori knowledge. The skull is first located at the most convex part of the occipital bone, since there are few other anatomic structures at this point compared with the region containing the TOB, and the pixels forming the skull at the most convex point can be located more robustly (see FIG. 4). Then the boundaries on both sides of the skull are traced to the end as a directional flow, assuming the ASM result is close to the occipital bone.

Figure 5:
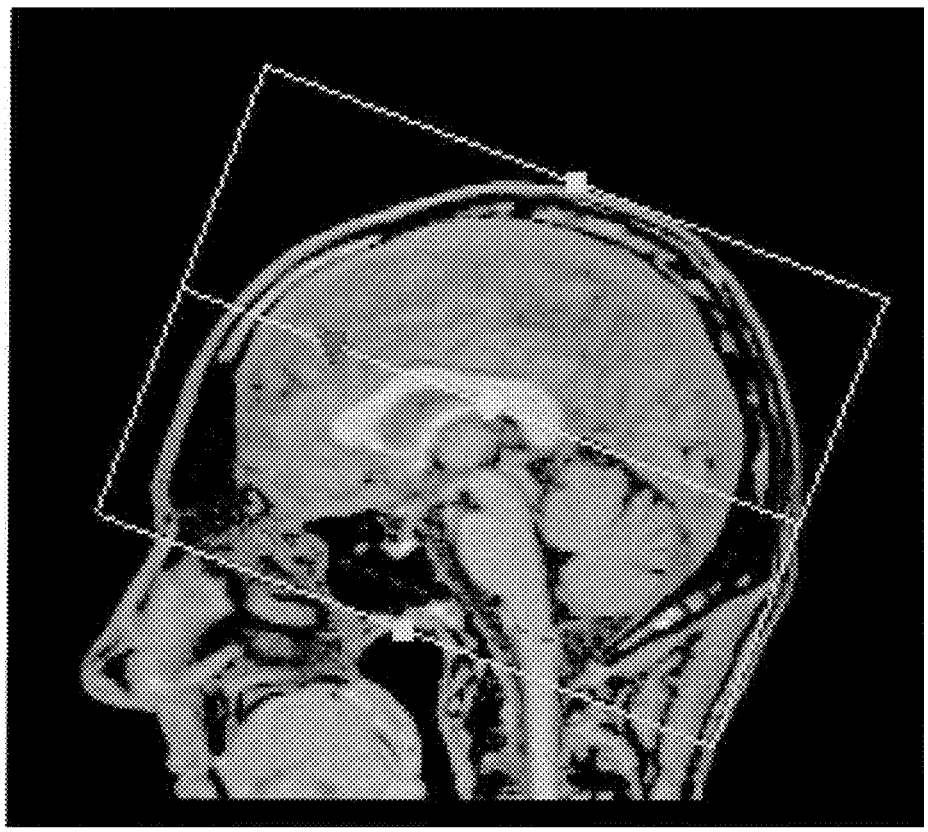
FIG. 5 illustrates identifying a crista galli (CG) and a tip of the occipital bone (TOB) on the re-sampled MSP image, in accordance with an exemplary embodiment of the present invention.

The bone marrow, which is located in the middle of the skull, has a similar intensity as the structures surrounding the occipital bone, such as brain on the anterior side and muscle and fat on the posterior side. Therefore, if the bone marrow appears large enough to occupy the entire space of the skull on the MR image, the boundary tracing along the occipital bone can be stopped before it reaches the TOB, like water being blocked in a jammed pipe. The present exemplary embodiment of the invention tackles this problem using a priori knowledge to guide the directional flow through the blockage from bone marrow. FIG. 5 gives the detection result of the CG and the TOB.

For example, as shown in FIG. 5, the anterior end of the dotted line is the CG, and the posterior end of the dotted line is the TOB. The rectangle with solid boundary is the slice package aligned based on the CG-TOB line. The solid line located in the middle of the slice package represents the middle transverse slice.

1.3 Transformation Matrix Calculation

In this section, we will first introduce the two coordinate systems used in our work, then we will describe how the transformation of alignment is calculated by anatomical landmarks.

1.3.1 Standard Coordinate System and Voxel Coordinate System

Figure 6:
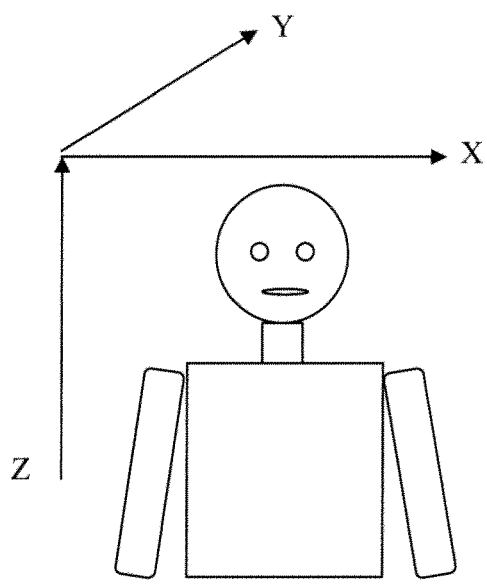
FIG. 6 is a diagram illustrating a definition of a conventional Digital Imaging and Communications in Medicine (DICOM) coordinate system.

The DICOM coordinate system, which is commonly used for medical imaging, is defined as shown in FIG. 6. However, the DICOM standard is vague on the precise definition of axis orientation and origin location. We thus further define a standardized coordinate system $(X_S, Y_S, Z_S)$ with respect to anatomical landmarks. Our standardized coordinate system is defined so that the equation for MSP is $X_S=0$. This definition means that the MSP is the $Y_S Z_S$ plane in the standardized coordinate system. The origin $O_S$ of the standardized coordinate system is defined so that the center of the scan volume is the center of the brain. The calculation of the center of the brain will be described hereinafter in section 1.3.2.2.

The alignment transformation matrix $M_{VS}$ transforms the voxel coordinate system $(X_V, Y_V, Z_V)$ of the current scan to the standardized coordinate system $(X_S, Y_S, Z_S)$, that is, $$\begin{bmatrix} X_S \\ Y_S \\ Z_S \\ 1 \end{bmatrix} = M_{VS} \begin{bmatrix} X_V \\ Y_V \\ Z_V \\ 1 \end{bmatrix} \quad \text{Equation 1}$$

Therefore, by multiplying $M_{VS}$ with the position and orientation of the 3D localizer volumes, we can obtain the scanning parameters for diagnostic scans whose voxel coordinate system is coincident with the standardized coordinate system. Since this system is defined by anatomic landmarks it allows for the acquisition of standardized and reproducible diagnostic scans for different MR studies and different patients.

1.3.2 Calculation of Transformation Matrix $M_{VS}$

Let $M_{SV} = M_{VS}^{-1}$, from Eq. 1 we have $$\begin{bmatrix} X_V \\ Y_V \\ Z_V \\ 1 \end{bmatrix} = M_{VS}^{-1} \begin{bmatrix} X_S \\ Y_S \\ Z_S \\ 1 \end{bmatrix} = M_{SV} \begin{bmatrix} X_S \\ Y_S \\ Z_S \\ 1 \end{bmatrix}$$

To calculate matrix $M_{SV}$, we translate the coordinate system to make the origin located in the middle of the brain, that is, $$\left( \begin{bmatrix} X_V \\ Y_V \\ Z_V \\ 1 \end{bmatrix} - T_{C\_V} \right) = M_{C\_SV} \left( \begin{bmatrix} X_S \\ Y_S \\ Z_S \\ 1 \end{bmatrix} - T_{C\_S} \right) \quad \text{Equation 2}$$

where $T_{C\_S}$ and $T_{C\_V}$ are the translation vectors. If we let the scan field of view (FOV) on the three directions in the standard coordinate system be equal to the FOV in voxel coordinate system, then we will have $$T_{C\_S} = T_{C\_V} = \frac{1}{2}[W_X, W_Y, W_Z]^t = T_C,$$

where $W_X$, $W_Y$, and $W_Z$ are the scan size on the X, Y, and Z directions.

$M_{C\_SV}$ is a composition of rotation and translation. Let the rotation matrix be given by $$R_{C\_SV} = \begin{bmatrix} r_{11} & r_{12} & r_{13} \\ r_{21} & r_{22} & r_{23} \\ r_{31} & r_{32} & r_{33} \end{bmatrix}$$

and the translation matrix be given by $$T_{C\_SV} = \begin{bmatrix} t_x \\ t_y \\ t_z \end{bmatrix}$$

Then we have $$M_{C\_SV} = \begin{bmatrix} 1 & 0 & 0 & t_x \\ 0 & 1 & 0 & t_y \\ 0 & 0 & 1 & t_z \\ 0 & 0 & 0 & 1 \end{bmatrix} \times \begin{bmatrix} r_{11} & r_{12} & r_{13} & 0 \\ r_{21} & r_{22} & r_{23} & 0 \\ r_{31} & r_{32} & r_{33} & 0 \\ 0 & 0 & 0 & 1 \end{bmatrix} = \quad \text{Equation 3}$$

$$\begin{bmatrix} r_{11} & r_{12} & r_{13} & t_x \\ r_{21} & r_{22} & r_{23} & t_y \\ r_{31} & r_{32} & r_{33} & t_z \\ 0 & 0 & 0 & 1 \end{bmatrix}$$

Substituting Equation 3 into Equation 2, and letting $$\begin{bmatrix} X_{C\_V} \\ Y_{C\_V} \\ Z_{C\_V} \end{bmatrix} = \begin{bmatrix} X_V \\ Y_V \\ Z_V \end{bmatrix} - T_C$$

and $$\begin{bmatrix} X_{C\_S} \\ Y_{C\_S} \\ Z_{C\_S} \end{bmatrix} = \begin{bmatrix} X_S \\ Y_S \\ Z_S \end{bmatrix} - T_C,$$

we get an equivalent equation, $$\begin{bmatrix} X_{C\_V} \\ Y_{C\_V} \\ Z_{C\_V} \end{bmatrix} = \quad \text{Equation 4}$$

$$R_{C\_SV} \begin{bmatrix} X_{C\_S} \\ Y_{C\_S} \\ Z_{C\_S} \end{bmatrix} + T_{C\_SV} = \begin{bmatrix} r_{11} & r_{12} & r_{13} \\ r_{21} & r_{22} & r_{23} \\ r_{31} & r_{32} & r_{33} \end{bmatrix} \begin{bmatrix} X_{C\_S} \\ Y_{C\_S} \\ Z_{C\_S} \end{bmatrix} + \begin{bmatrix} t_x \\ t_y \\ t_z \end{bmatrix}$$

1.3.2.1 Calculation of rotation matrix $R_{C\_SV}$

The rotation matrix $R_{C\_SV}$ can be decomposed into three rotations about axis $X_{C\_S}$, $Y_{C\_S}$, and $Z_{C\_S}$, that is, $R_{C\_SV} = R_{C\_SV}(\chi) R_{C\_SV}(\beta) R_{C\_SV}(\alpha)$, where $R_{C\_SV}(\alpha)$ is the rotation about $X_{C\_S}$ axis, with rotation angle $\alpha$, $$R_{C\_SV}(\alpha) = \begin{bmatrix} 1 & 0 & 0 \\ 0 & \cos\alpha & -\sin\alpha \\ 0 & \sin\alpha & \cos\alpha \end{bmatrix},$$

$R_{C\_SV}(\beta)$ is the rotation about $Y_{C\_S}$ axis, with rotation angle $\beta$, $$R_{C\_SV}(\beta) = \begin{bmatrix} \cos\beta & 0 & \sin\beta \\ 0 & 1 & 0 \\ -\sin\beta & 0 & \cos\beta \end{bmatrix},$$

and $R_{C\_SV}(\chi)$ is the rotation about $Z_{C\_S}$ axis, with rotation angle $\chi$, $$R_{C\_SV}(\chi) = \begin{bmatrix} \cos\chi & -\sin\chi & 0 \\ \sin\chi & \cos\chi & 0 \\ 0 & 0 & 1 \end{bmatrix}. \quad \text{Equation 5}$$

$$R_{C\_SV} = R_{C\_SV}(\chi) R_{C\_SV}(\beta) R_{C\_SV}(\alpha) =$$

$$\begin{bmatrix} \cos\beta\cos\chi & \sin\alpha\sin\beta\cos\chi - \cos\alpha\sin\chi & \cos\alpha\sin\beta\cos\chi + \sin\alpha\sin\chi \\ \cos\beta\sin\chi & \sin\alpha\sin\beta\sin\chi + \cos\alpha\cos\chi & \cos\alpha\sin\beta\sin\chi - \sin\alpha\cos\chi \\ -\sin\beta & \sin\alpha\cos\beta & \cos\alpha\cos\beta \end{bmatrix}$$

Thus,

To calculate the rotation matrix, we need to determine the three rotation angles $\alpha$, $\beta$, and $\chi$. In our algorithm, the rotation angle $\chi$ about $Z_{C\_S}$ axis is first computed using the method proposed by Liu et al (Yanxi Liu, Robert T. Collins, and William E. Rothfus, "Robust Midsagittal plane extraction from normal and pathological 3-D neuroradiology images", IEEE Transactions on Medical Imaging, vol. 20, No. 3, March 2001).

In the translated standard coordinate system ($X_{C\_S} Y_{C\_S} Z_{C\_S}$), the MSP is represented by $X_{C\_S}=0$, and in the voxel coordinate system, the MSP can be represented as the following:

$$aX_{C\_V} + bY_{C\_V} + cZ_{C\_V} + d = 0 \quad \text{Equation 6}$$

Then the 2D line of MSP on ith transverse slice in the voxel coordinate system is the intersection of the MSP (Equation 6) and plane $Z_{C\_V} = z_i$, that is, $$aX_{C\_V} + bY_{C\_V} + cz_i + d = 0$$

Equivalently, $$X_{C\_V} = -\frac{b}{a} Y_{C\_V} - \frac{cz_i + d}{a} = k_1 Y_{C\_V} - \frac{cz_i + d}{a} \quad \text{Equation 7}$$

From Equation 4, we have $$\begin{bmatrix} X_{C\_S} \\ Y_{C\_S} \\ Z_{C\_S} \end{bmatrix} = R_{C\_SV}^{-1} \left( \begin{bmatrix} X_{C\_V} \\ Y_{C\_V} \\ Z_{C\_V} \end{bmatrix} - T_{C\_SV} \right) = R_{C\_SV}^{t} \left( \begin{bmatrix} X_{C\_V} \\ Y_{C\_V} \\ Z_{C\_V} \end{bmatrix} - T_{C\_SV} \right) \quad \text{Equation 8}$$

with $X_{C\_S} = 0$, and we have $$\cos\beta\cos\chi X_{C\_V} + \cos\beta\sin\chi Y_{C\_V} - \sin\beta Z + d' = 0$$

where $d' = -[\cos\beta\cos\chi, \cos\beta\sin\chi, -\sin\beta] \cdot T_{C\_SV}$. Provided $|\beta| \neq 90°$ and $|\chi| \neq 90°$ (otherwise, we need to transpose the scan volume to obtain a desired orientation), and $\cos\beta \neq 0$ and $\cos\chi \neq 0$, we can then calculate $\chi$ by combining Equation 7 and Equation 8.

$$k_1 = \frac{-\sin\chi}{\cos\chi} \Rightarrow \chi = a\tan(-k_1) \quad \text{Equation 9}$$

where $k_1$ is the slope of MSP line $L_1: X_{C\_V} = k_1 Y_{C\_V} + c_1$ calculated on a transverse slice.

Using the result in Equation 9, we can further compute $\beta$ by giving the intersection line function of the MSP (Equation 6) and jth coronal slice $Y_{C\_V} = y_j$ as the following:

$$aX_{C\_V} + by_j + cZ_{C\_V} + d = 0 \Rightarrow X_{C\_V} = k_2 Z_{C\_V} - \frac{by_j + d}{a} \quad \text{Equation 10}$$

Provided $\cos\beta \neq 0$ and $\cos\chi \neq 0$, we can calculate $\beta$ by combining Equation 8 and Equation 10, $$k_2 = \frac{\tan\beta}{\cos\chi} \Rightarrow \beta = a\tan(k_2 \cos\chi) \quad \text{Equation 11}$$

where $k_2$ is the slope of MSP line $L_2: X_{C\_V} = k_2 Z_{C\_V} + c_2$ calculated on a coronal slice.

The rotation angle $\alpha$ can be directly calculated on the re-sampled MSP by the anatomical landmarks CG-TOB. Let $L_3: Z_{C\_V} = k_3 Y_{C\_V} + c_3$ denote the CG-TOB line on the re-sampled MSP, then $$\alpha = a\tan(k_3) \quad \text{Equation 12}$$

1.3.2.2 Calculation of Translation Matrix $T_{C\_SV}$

In the translated standard coordinate system $X_{C\_S} Y_{C\_S} Z_{C\_S}$ we set the center of the brain as the origin, then from Equation 4 we have $$\begin{bmatrix} x_V \\ y_V \\ z_V \end{bmatrix} = R_{C\_SV} \begin{bmatrix} 0 \\ 0 \\ 0 \end{bmatrix} + T_{C\_SV} = T_{C\_SV} \quad \text{Equation 13}$$

The coordinate $[x_V, y_V, z_V]^t$ of brain center in the translated voxel coordinate system can be calculated by the two MSP intersection lines on the transverse and coronal slices, $L_1: X_{C\_V} = k_1 Y_{C\_V} + c_1$ and $L_2: X_{C\_V} = k_2 Z_{C\_V} + c_2$. Let $p_1 \in L_1$, $p_2 \in L_2$, and the distance between $p_1$ and $p_2$ is the shortest among all the points on $L_1$ and $L_2$. Then $$\begin{bmatrix} x_V \\ y_V \\ z_V \end{bmatrix} = \frac{1}{2}(p_1 + p_2) - T_C$$

2.3.2.3 Calculation of Output Rigid-Body Transformation Matrix $M_{VS}$

Again, from Equation 4, we have $$\begin{bmatrix} X_S \\ Y_S \\ Z_S \end{bmatrix} = R_{C\_SV}^{1} \begin{bmatrix} X_V \\ Y_V \\ Z_V \end{bmatrix} + (T_C - R_{C\_SV}^{t}(T_C + T_{C\_SV})).$$

Then the final output matrix $M_{VS}$ is $$M_{VS} = \begin{bmatrix} R_{C\_SV}^{t} & T_C - R_{C\_SV}^{t}(T_C + T_{C\_SV}) \\ 0 \quad 0 \quad 0 & 1 \end{bmatrix}.$$

where $R_{C\_SV}^{t}$ and $T_{C\_SV}$ can be calculated by Equation 5 and Equation 13, and $$T_C = \frac{1}{2}[W_X, W_Y, W_Z]^{t},$$

with $W_X$, $W_Y$, and $W_Z$ are the scan FOV in the X, Y, and Z directions.

Diagnostic scan planning is embodied by a slice package that consists of a set of slices (e.g., a stack of images) each having its own geometry description, e.g., center location, orientation, width and height. The slice package is a predefined slice package for a standard positioned patient and is generally available at most medical diagnostic centers. The standard positioned patient means that the patient is ideally positioned to be coincident with the standardized coordinate system $(X_S, Y_S, Z_S)$, which is defined with respect to anatomical landmarks so that the equation for the MSP is $X_S = 0$ and the CG-TOB line on the MSP is coincident with the $X_S$ axis. The origin of $O_S$ of the standardized coordinate system is defined so that the center of the scan volume is the center of the brain. Let $M_{VS}$ denote the transformation matrix, $G_{Slice}$-$p_a$ denote the slice package, then $M_{VS} \times G_{Slice}$-$p_a$ will be the transformed slice package for the diagnostic scan, that is, the scan plan for the current diagnostic scan to be performed on the patient. In this manner, the scan plan for the current patient becomes aligned with the standardized coordinate system to allow for the acquisition of standardized and reproducible diagnostic scans.

2. Experimental Results

Figure 7:
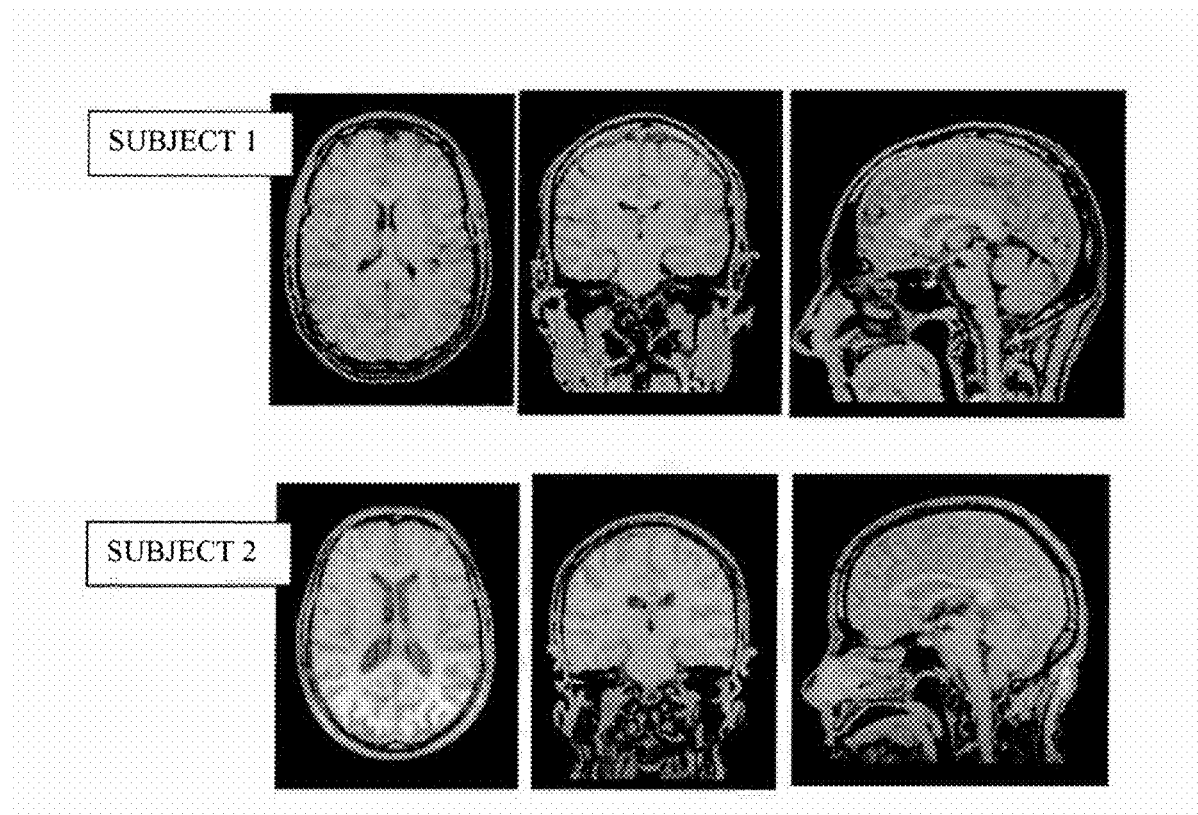
FIG. 7 illustrates an example of standardized imaging proved by coincident anatomical structures on coronal, transverse, and sagittal images from different patients, in accordance with an exemplary embodiment of the present invention.

The present invention described above provides standardized imaging among different patients for comparison and statistical analysis within populations. In FIG. 7, after applying the alignment transformation matrix to original 3D localizer scans, standardized imaging is proved by the coincident anatomic structures on the corresponding transverse, coronal and sagittal images from two patients.

As described above, the present invention is directed to an automatic method to align brain scans directly without using anatomic landmarks. This alignment method is insensitive to individual anatomy and pathology, and is thus able to standardize imaging for different patients and deliver reproducible results for follow-up studies.

A system in which exemplary embodiments of the present invention may be implemented will now be described with reference to FIG. 8.

Figure 8:
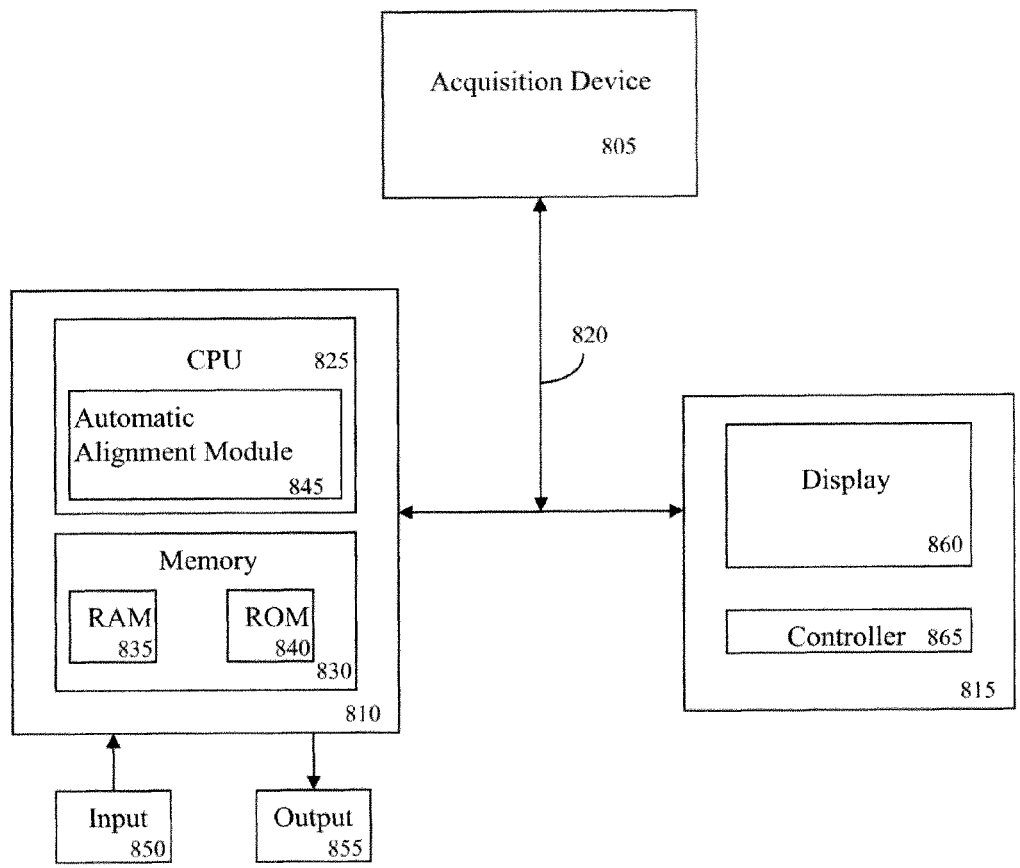
FIG. 8 is a block diagram of a system in which exemplary embodiments of the present invention may be implemented.

As shown in FIG. 8, the system includes an acquisition device 805, a personal computer (PC) 810 and an operator's console 815 connected over a wired or wireless network 820. The acquisition device 805 may be an MR scanner or an ultrasound scanner.

The PC 810, which may be a portable or laptop computer, a medical diagnostic imaging system or a picture archiving communications system (PACS) data management station, includes a central processing unit (CPU) 825 and a memory 830 connected to an input device 850 and an output device 855. The CPU 825 includes an automatic alignment module 845 that includes program code for executing methods in accordance with exemplary embodiments of the present invention.

The memory 830 includes a random access memory (RAM) 835 and a read-only memory (ROM) 840. The memory 830 can also include a database, disk drive, tape drive, etc., or a combination thereof. The RAM 835 functions as a data memory that stores data used during execution of a program in the CPU 825 and is used as a work area. The ROM 840 functions as a program memory for storing a program executed in the CPU 825. The input 850 is constituted by a keyboard, mouse, etc., and the output 855 is constituted by a liquid crystal display (LCD), cathode ray tube (CRT) display, printer, etc.

The operation of the system can be controlled from the operator's console 815, which includes a controller 865, e.g., a keyboard, and a display 860. The operator's console 815 communicates with the PC 810 and the acquisition device 805 so that image data collected by the acquisition device 805 can be rendered by the PC 810 and viewed on the display 860. The PC 810 can be configured to operate and display information provided by the acquisition device 805 absent the operator's console 815, by using, e.g., the input 850 and output 855 devices to execute certain tasks performed by the controller 865 and display 860.

The operator's console 815 may further include any suitable image rendering system/tool/application that can process digital image data of an acquired image dataset (or portion thereof) to generate and display images on the display 860. More specifically, the image rendering system may be an application that provides rendering and visualization of medical image data, and which executes on a general purpose or specific computer workstation. The PC 810 can also include the above-mentioned image rendering system/tool/application.

It is to be understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It should also be understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It is to be further understood that the above description is only representative of illustrative embodiments. For convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method to automatically align magnetic resonance (MR) brain scans for diagnostic scan planning, comprising:
   acquiring a three-dimensional (3D) localizer image of a patient;
   selecting a two-dimensional (2D) coronal view and a 2D transverse view from the localizer image;
   identifying a mid-sagittal plane (MSP) line in each of the coronal and transverse views and calculating a 3D MSP based on the MSP lines;
   reconstructing the localizer image based on an equation for the 3D MSP to obtain an image of the MSP of the patient's brain;
   identifying crista galli (CG) and tip of the occipital bone (TOB) in the image of the MSP of the patient's brain;
   calculating a transformation matrix based on the MSP, CG and TOB in the image and using the transformation matrix to obtain a scan plan for the patient; and
   outputting the scan plan for the patient,
   wherein the step of identifying an MSP line in each of the coronal and transverse views comprises:
   detecting a position of the patient's head by fitting an ellipse to each of the coronal and transverse views that maximizes an image gradient magnitude in a boundary region of the ellipse;
   establishing a symmetrical axis which minimizes a difference between the coronal and transverse views on either side of the symmetrical axis;
   characterizing low intensity pixels in the coronal and transverse views by using smoothed local differential operators;
   finding pixels in the coronal and transverse views that form a space between hemispheres in each of the coronal and transverse views; and
   running a linear regression with robust weights to define a line in each of the coronal and transverse views that best separates the two hemispheres, wherein the line is the MSP line.

2. The method of claim 1, wherein the CG is identified by:
   applying an active shape model (ASM) to segment the patient's skull and other anatomic structures around the patient's brain.

3. The method of claim 2, wherein the TOB is identified by:
   searching for low intensity voxels in the segmented skull, wherein the low intensity voxels identify a most convex part of the OB; and
   tracing boundaries on both sides of the skull to an end of the OB, which is the TOB.

4. The method of claim 1, wherein the scan plan for the patient is obtained by multiplying the transformation matrix by a standard slice package.

5. The method of claim 4, wherein the standard slice package includes a set of image slices with geometry descriptions to be acquired from the patient in a standard coordinate system.

6. The method of claim 1, further comprising:
   executing the scan plan for the patient.

7. A system to automatically align magnetic resonance (MR) brain scans for diagnostic scan planning, comprising:
   a memory device for storing a program;
   a processor in communication with the memory device, the processor operative with the program to:
   acquire a three-dimensional (3D) localizer image of a patient;
   select a two-dimensional (2D) coronal view and a 2D transverse view from the localizer image;
   identify a mid-sagittal plane (MSP) line in each of the coronal and transverse views and calculate a 3D MSP based on the MSP lines;
   reconstruct the localizer image based on an equation for the 3D MSP to obtain an image of the MSP of the patient's brain;
   identify crista galli (CG) and tip of the occipital bone (TOB) in the image of the MSP of the patient's brain;
   calculate a transformation matrix based on the MSP, CO and TOB in the image and using the transformation matrix to obtain a scan plan for the patient; and
   output the scan plan for the patient,
   wherein the processor is further operative with the program when identifying an MSP line in each of the coronal and transverse views to:
   detect a position of the patient's head by fitting an eclipse to each of the coronal and transverse views that maximizes an image gradient magnitude in a boundary region of the ellipse;
   establish a symmetrical axis which minimizes a difference between the coronal and transverse views on either side of the symmetrical axis;
   characterize low intensity pixels in the coronal and transverse views by using smoothed local differential
   find pixels in the coronal and transverse views that form a space between hemispheres in each of the coronal and transverse views; and
   run a linear regression with robust weights to define a line in each of the coronal and transverse views that best separates the two hemispheres, wherein the line is the MSP line.

8. The system of claim 7, wherein the CG is identified by applying an active shape model (ASM) to segment the patient's skull and other anatomic structures around the patient's brain.

9. The system of claim 8, wherein the TOB is identified by searching for low intensity voxels in the segmented skull, wherein the low intensity voxels identify a most convex part of the OB; and
   tracing boundaries on both sides of the skull to an end of the OB, which is the TOB.

10. The system of claim 7, wherein the scan plan for the patient is obtained by multiplying the transformation matrix by a standard slice package.

11. The system of claim 10, wherein the standard slice package includes a set of image slices with geometry descriptions to be acquired from the patient in a standard coordinate system.

12. The system of claim 7, wherein the processor is further operative with the program to:
    execute the scan plan for the patient.

13. A non-transitory computer readable medium tangibly embodying a program of instructions executable by a processor to perform method steps to automatically align magnetic resonance (MR) brain scans for diagnostic scan planning, the method steps comprising:
    acquiring a three-dimensional (3D) localizer image of a patient;
    selecting a two-dimensional (2D) coronal view and a 2D transverse view from the localizer image;
    identifying a mid-sagittal plane (MSP) line in each of the coronal and transverse views and calculating a 3D MSP based on the MSP lines;
    reconstructing the localizer image based on an equation for the 3D MSP to obtain an image of the MSP of the patient's brain;
    identifying crista galli (CG) and tip of the occipital bone (TOB) in the image of the MSP of the patient's brain;
    calculating a transformation matrix based on the MSP, CG and TOB in the image and using the transformation matrix to obtain a scan plan for the patient; and
    outputting the scan plan for the patient,
    wherein the step of identifying an MSP line in each of the coronal and transverse views comprises:
    detecting a position of the patient's head by fitting an ellipse to each of the coronal and transverse views that maximizes an image gradient magnitude in a boundary region of the ellipse;
    establishing a symmetrical axis which minimizes a difference between the coronal and transverse views on either side of the symmetrical axis;
    characterizing low intensity pixels in the coronal and transverse views by using smoothed local differential operators;
    finding pixels in the coronal and transverse views that form a space between hemispheres in each of the coronal and transverse views; and
    running a linear regression with robust weights to define a line in each of the coronal and transverse views that best separates the two hemispheres, wherein the line is the MSP line.

14. The computer readable medium of claim 13, wherein the CG is identified by:
    applying an active shape model (ASM) to segment the patient's skull and other anatomic structures around the patient's brain.

15. The computer readable medium of claim 14, wherein the TOB is identified by:
- searching for low intensity voxels in the segmented skull, wherein the low intensity voxels identify a most convex part of the OB; and
- tracing boundaries on both sides of the skull to an end of the OB, which is the TOB.

16. The computer readable medium of claim 13, wherein the scan plan for the patient is obtained by multiplying the transformation matrix by a standard slice package.

17. The computer readable medium of claim 16, wherein the standard slice package includes a set of image slices with geometry descriptions to be acquired from the patient in a standard coordinate system.

18. The computer readable medium of claim 13, wherein the method further comprises:
- executing the scan plan for the patient.

* * * * *